United States Patent
Raisz et al.

(10) Patent No.: US 8,445,548 B2
(45) Date of Patent: May 21, 2013

(54) PROCESS FOR THE PREPARATION OF SYNGAS AND METHANOL FROM ORGANIC WASTES

(76) Inventors: Iván Raisz, Felsözsolca (HU); István Barta, Nyiregyháza (HU)

( * ) Notice: Subject to any disclaimer, the term of this patent is extended or adjusted under 35 U.S.C. 154(b) by 216 days.

(21) Appl. No.: 12/933,921

(22) PCT Filed: Apr. 2, 2009

(86) PCT No.: PCT/HU2009/000029
§ 371 (c)(1),
(2), (4) Date: Oct. 26, 2010

(87) PCT Pub. No.: WO2009/122225
PCT Pub. Date: Oct. 8, 2009

(65) Prior Publication Data
US 2011/0039956 A1   Feb. 17, 2011

(30) Foreign Application Priority Data

Apr. 2, 2008 (HU) .................................. P 0800209

(51) Int. Cl.
*C07C 27/00* (2006.01)

(52) U.S. Cl.
USPC ............ 518/702; 518/700; 518/703; 518/704

(58) Field of Classification Search
USPC .......................................... 518/700, 702–704
See application file for complete search history.

(56) References Cited

U.S. PATENT DOCUMENTS

| | | | |
|---|---|---|---|
| 5,104,419 A | 4/1992 | Funk | |
| 6,090,355 A | 7/2000 | Winkler et al. | |
| 2002/0095866 A1 | 7/2002 | Hassett | |
| 2003/0158270 A1 | 8/2003 | Mahajan | |

FOREIGN PATENT DOCUMENTS

| | | |
|---|---|---|
| EP | 0 790 291 A2 | 8/1997 |
| EP | 0 924 288 A2 | 6/1999 |
| EP | 0 979 857 A2 | 2/2000 |
| WO | 01/38456 A1 | 5/2001 |
| WO | 2007/005126 A1 | 1/2007 |

OTHER PUBLICATIONS

Kirjavainen et al.: "Small-scale biomass CHP technologies", Processes and Finnish District Heating, 2004.
Unknown: "Feasibility Phase Project for Biomass-Derived Alcohols for Automotive and Industrial Uses"; BAL-Fuels Project, 1997.
Grabowski: "Biomass Thermochemical Conversion OBP Efforts", 2004.
Walt: "The BioMax<™> A new biopower option for distributed generation and CHP", IEEE, 2004.

*Primary Examiner* — Jafar Parsa
(74) *Attorney, Agent, or Firm* — Jason D. Voight

(57) ABSTRACT

The invention is related to the preparation of low-tar syngas from organic wastes and optionally to the preparation of methanol from the syngas or from the separated carbon dioxide. The process is characterized by introducing the secondary raw material comprising preferably solid communal waste, sludge and/or biomass waste into a double-flow one-body generator, comprising an inner pyrolysing, oxidizing and reducing zone and converting the obtained pyrolysis coke, pyrolysis water and tar formed by the aid of the heat content of the gas flowing upwards in the outer gas space by blowing oxygen into the fix-bed, to a raw syngas comprising carbon dioxide, carbon monoxide and hydrogen, on the fix bed of the pyrolysis coke and optionally a liquid containing liquid hydrocarbons or a powder of high carbon content are added in order to control the temperature and hydrohalides are removed from the obtained raw syngas on a calcium carbonate bed at 200-700° C., the heat content of the raw syngas is utilized, carbon dioxide is removed by a method known per se, and carbon dioxide is converted to methanol by using an external hydrogen source and optionally the obtained syngas is also converted to methanol by a method known per se.

12 Claims, 1 Drawing Sheet

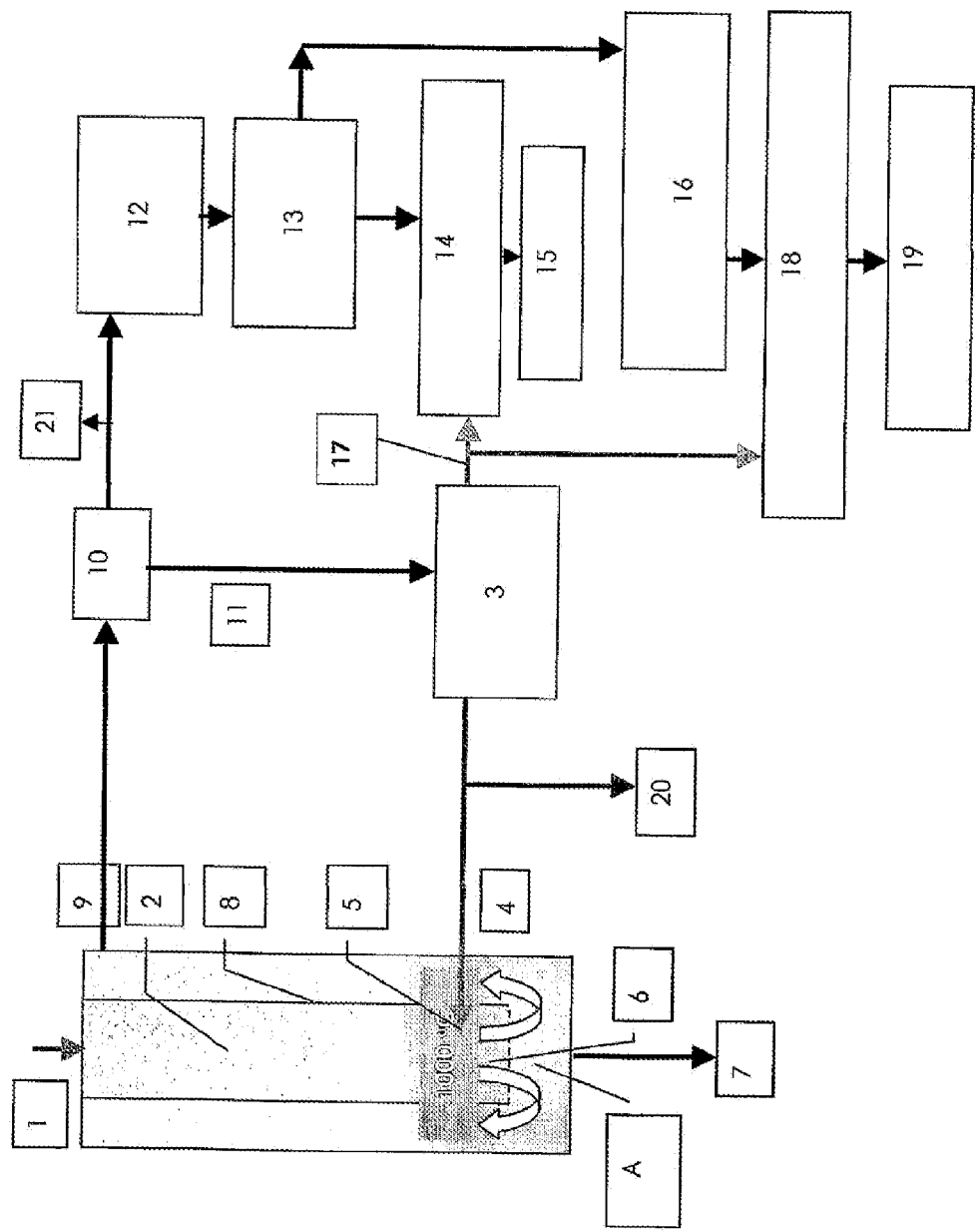

PROCESS FOR THE PREPARATION OF SYNGAS AND METHANOL FROM ORGANIC WASTES

This is the National Phase of PCT/HU2009/000029, filed Apr. 2, 2009.

TECHNICAL FIELD

The present invention is related to the preparation of low-tar syngas from organic wastes and to the preparation of methanol from the syngas or from the separated carbon dioxide.

BACKGROUND OF THE INVENTION

Most countries all over the world have become more or less dependent in the last decades with regards to the various energy sources to be found in the outer spaces. This dependency is all the more query, as a significant occurrence of the fossil fuels can be found on places, which have been under a burden of conflict for a long time.

Due to the excessive use of the conventional energy carriers, the increase of the carbon dioxide content of the atmosphere can be shown, accompanied by the unfavourable change of the weather together with other glasshouse gases.

As a further environmental problem the amount of certain agricultural and communal and other industrial wastes is increasing, bound unambiguously to the human activities in our age, and the present treatment of said wastes also result in the considerable increase of the amount of glass-gases in addition to other environmental problems. We can say that the continuous increase of the amount of said gases with almost unchanged composition can be interpreted as a renewing raw material accompanying human activity.

In Hungary in the communal waste one can find about 2.5 million tons/year of biodegradable organic waste. About 50% of this is amount is degraded to carbon dioxide and methane in the shoot. It means 800 thousands tons/year of carbon dioxide and 400 thousands tons/year of methane load in the atmosphere. The partially dehydrated (unburnt) waste water sludge load on the soil is 1.5 million tons/year, meaning 90.000 tons/year of carbon dioxide and 50.000 tons/year of methane load in the atmosphere. As a result of the above waste deposition process the equivalent value of the carbon dioxide of the emitted glass-gases in the atmosphere is 10 million tons/year. The yearly amount of solid, organic, biologically non-biodegradable waste of industrial origin delivered to the communal waste depository is also 2.5 million pro year. The ratios are similar in other countries of the world. The manufacture of fuels of biological origin and the production of the corresponding necessary syngas has widely spread all over the world.

Thorough lifecycle analysis (LCA) tests have shown on one hand the energetically negative or in some cases just positive balance of the today used processes, and on the other hand the increasing glasshouse effect related to one unit of utilizable energy considering the used energy and intermediates of the processes. (Raisz-Emmer: Effective Carbon Rate . . . , EMEC7 Brno 2006).

The authors of the FP7(7. framework programme) have presumably recognized this problem, when they announced the subject: 2007.3.2.5. Synthetic biofuels via gasification collaborative.

The syngas production from biomass has been already carried out in several countries, the syngas was used in gas motors for producing electrical or thermal energy (Case Study: 2 $MW_{el}$ biomass gasification plant in Güssing. EC Contract No. NNE5/2002/52:OPET CHP/DH Cluster), or Fischer-Tropsch liquid (Choren Program Freiberg) or in some cases methanol has been prepared. In most of the cases the used biomass is a primary forest product derived from forests considered ready for woodcutting, i.e. raw tree-trunk. This raw material has suppressed the furniture production from wood on the market, the use of plastics has spread instead, the energy investment of which several times exceeds the energy obtained from the burnt/pyrolysed wood.

Syngas producing plants have appeared, which utilize only a small part of the wastes, i.e. the non-selectively collected plastic raw materials (Corenso United Oy Ltd., Finland).

According to WO2007005126 syngas is produced from hydrocarbons, and syngas is then converted to methanol. In US2003158270 a catalytic system is disclosed which can be used at a relatively low temperature and pressure, but the production of syngas is not disclosed.

In the Battelle Columbus gasification system (*BAL-Fuels Project,* 1997) the formed carbon dioxide is disposed of the system and draught is used, reducing thereby the concentration of the useful components of syngas. Its special tar degrading system requires unnecessary operational and investment costs. HTW technology uses wood as raw material and the gasification system is operated at 27 bar. The oxygen blown into the system is obtained from the air separator, nitrogen is used only for drying. In the course of the HTW process a fluid-bed reactor is used, and the obtained gas mixture strongly contaminated with solid particles and tar vapours, said components can separated by an expensive process.

According to EP 0790291 B1 a thermally pre-treated and/or compressed waste is used and gasification is carried out on a fluid bed reactor at a temperature above 2000° C. When using fluid-bed reactors, the solid particles carried away with the gases, have to be removed requiring an expensive separation. In U.S. Pat. No. 5,104,419 the gasification is carried out with a 60:40-40:60 mixture of oxygen and carbon dioxide in a reactor operated at 800-1000° C., there is no heat utilization from the syngas, but tar and other oily products are formed, which have to be treated and carbon dioxide has to be removed from the system. A common feature of the processes in a fluid bed reactor is that a significant part of the fed solid particles stays in the reactor only sufficient for the pyrolysis and the obtained pyrolysis products as the pyrolysis tar cannot be further degraded or take part in the gasification.

On the basis of their widespread experiences Veba Oil technology has elaborated a process for the preparation of secondary raw materials of communal wastes, suitable for the gasification of the products of the previous procedures, and it includes a cracking process [Redepenning, K.: Valorisation des déchets—faisabilité du recyclage chimique. Informations Chimie, 372. (1995) p. 95-99.]. The plastics depolymerize when heated up to 380° C. Upon cooling the formed vapours, the gases and the condensed material are separated, latter is degraded to an oily and an aqueous layer. The isolated depolymerization makes it possible to remove the obtained hydrogen halides from the halo-containing plastic materials by washing before further processing. In the pyrolysis step pyrolysis takes place in the pyrolysis step based on a 70 years old experience in a modernized rotating oven, whereafter the residual pyrolysis burnt coal is introduced to the gasification system after having ground it to dust. The pyrolysis oil is recycled to the pyrolysis reactor if necessary or used in the gasification system. For the gasification a reactor is used which has been operated for 30 years, delivering 16.000 m³ of syngas. Syngas is prepared in a gasification plant from wastes obtained in the course of pyrolysis and other technologies. Since 1972 in Veba 4 gasification lines have been operated at a capacity of about 60 tons/hour. 16.000 Nm³ syngas are produced in a system of a pressure of 60 bar. The pyrolysing system is not suitable for the treatment of highly humid wastes, the gasification is mainly carried out by using air, and the pressure is high in each unit, requiring plus investment and operation costs and the safety risk is increased.

An international comparison may be based on studying 2004 Gasification Database Gasification Plant Datasheets, summarizing the gasification systems operating and under construction in the year of edition. An important part of the operative processes deals with the gasification of petrol coke of oil industry (Shell development) and another part deals with the gasification of biomass and communal waste. A common element of said processes is the use of a brown coal stabilizer component, increasing significantly the sulphur content of the obtained gas, leading to a considerable increase of investment and operation costs.

In the course of the Green Recycle process the used air contains more than 50% of nitrogen, and tar and oil side products, requiring further equipments for the processing or dangerous wastes/side products are obtained.

According to the Primenergy/PRM process gasification is carried out by using air and the gases leaving the generator contain a significant amount of tar vapours and inert nitrogen being adverse from the point of view of utilization.

According to Community Power BioMAX process also air is fed to the system, but the combustion zone is before the reduction zone. The obtained gases also contain tar vapours and inert nitrogen being adverse from the point of view of utilization. According to the Fluid-Bed Gasifier (EPI, Carbona, MTCI) process a mixture of air and water vapour is blown into the biomass grist forming the fluid-bed. In this process the preparation of the solid material is expensive and may be the source of many mistakes and at the same time the obtained gas contains vapour gases, flue ashes and inert nitrogen being adverse from the point of view of utilization. The FERCO process helps to hold back the solid phase but at the same time the other disadvantages of the fluid processes are maintained.

SUMMARY OF THE INVENTION

Due to the unequal retention time in the fluid-bed reactors a significant amount of tar leaves the reactor, that makes the process difficult to handle and expensive, and also the thermic pre-treatment (drying) is expensive and polluting from energetic point of view. Therefore the aim of the invention was to prepare syngas with less energy and costs by eliminating the above disadvantages. We have found that the process according to the present invention solves this problem. The present invention is directed to the preparation of low-tar syngas from organic wastes and to the preparation of methanol from the syngas or from the separated carbon dioxide in a one-step system in a generator in one body. The obtained syngas is suitable for the preparation of methanol, Fischer-Tropsch fuel or other CO or $H_2$ based synthesis. The secondary raw material comprising mainly solid communal waste, waste sludge and/or biomass is introduced to a double flow generator in one body comprising an inner pyrolysing, oxidizing and reducing zone. The obtained pyrolysis coke, pyrolysis water and tar formed by the aid of the heat content of the gas flowing upwards in the outer gas space are, by blowing oxygen into the fix-bed at a pressure of 0.9-2 bar and with water vapour derived from drying and pyrolysis in the reactor space, converted to a raw gas comprising carbon dioxide, carbon monoxide and hydrogen, on the fix bed of the pyrolysis coke. The process is carried out at a temperature of 600-1200° C., preferably at 1000° C. One of the advantages of the process according to the present invention is that when carrying out the heat degradation of the biomass type materials, one has to consider that water is split off. Consequently water is available in the reactor system without direct adding water. When preparing the raw material, one has to determine the pre-drying composition, generating the appropriate water vapour amount needed for the water gas reaction. The obtained syngas is utilized in a special process for the preparation of methanol. One of the features of the present invention is that both from the formed syngas and from the carbon dioxide removed from the reaction mixture methanol is produced by using an external hydrogen source.

As a possibility to control the temperature we do not only blow oxygen to the coal/coke bed formed by the pyrolysis, but if necessary we make it possible to blow water vapour in order to reduce the temperature of the bed. In case of an undesired reduction of the temperature, we blow waste oils into the oxygen blast level, increasing thereby the heat-value of the reacting materials. In order to control the temperature a liquid hydrocarbon containing liquid or a high carbon containing powder are added and from the obtained crude syngas hydrohalides are removed at a temperature of 200-700° C. on a limestone bed, whereafter the heat content of the raw syngas is utilized and carbon dioxide is removed by a method known per se, the carbon dioxide is converted to methanol by the use of external hydrogen source and of the obtained syngas is also converted to methanol by a method known per se. By using a part of the purified gases in the gas motor the electric energy is provided which by decomposing water provides the oxygen to be injected into the generator into the fix bed, and the obtained hydrogen provides the appropriate CO-$H_2$ ratio in the methanol reactor. By storing the carbon dioxide extracted from the syngas by washing with water, it is converted to methanol by mixing it with hydrogen gas prepared by the aid of electric energy obtained from the periodically available renewed energy. Methanol is synthesized in a catalytic reactor under a pressure of 17-75 bar and at a temperature of 100-260° C.

The invention is based on the surprising fact that we have recognized that a suitable mixture of solid communal wastes, waste sludge and biomass wastes is capable, at temperatures higher than pyrolysis conditions already at atmospheric pressure in the presence of water vapour and by injecting oxygen, of ensuring such conditions, under which the conventional biomass waste materials can also be utilized (decomposed to syngas components), thus no dangerous wastes are formed except the vitrified float. It was further recognized that from the used starting materials without the utilization according to our invention, if they get into the waste depositories, glass-gases are formed in an amount of twice the weight of the equivalent carbon dioxide. Thus our process would result in a useful carbon proportion greater than one, even if a part of the syngas would not be used for the preparation of electric energy, by which via electrolysis we can prepare pure oxygen needed for achieving the high bed temperature in the generator and also prepare hydrogen needed to adjust the carbon monoxide and hydrogen ratio. A further advantage of the system is, that at the blowing level of the generator dangerous waste: hydrocarbons and water contaminated with hydrocarbons can be introduced serving as a base.

A further essential recognition was that when carbon dioxide is removed from the system at high pressure by an absorbing liquid of alkali carbonate, then it is not necessary to purify methanol obtained from the carbon monoxide-hydrogen mixture, as no water is formed.

The washed carbon dioxide is desorbed and stored in liquid state, until the renewed energy source ensures the hydrogen necessary for the conversion to methanol by electrolysis. The oxygen formed by electrolysis represents a value on the market. Water is already formed in the course of the reaction of carbon dioxide and hydrogen and is separated from methanol by selective condensation.

The hydrohalides formed due to the halogen content, are first removed from the crude generator gas whereafter the heat is utilized and the condensable components are separated and then hydrogen sulphide is also removed.

FIG. 1 illustrates the process according to the present invention without limiting the scope of the invention to the FIGURE.

References in the FIGURE are as follows:

A generator body
1 feed of the waste mixture
2 pyrolysis zone
3 electrolysis of water
4 oxygen feed
5 oxidation zone
6 reduction zone
7 removal of melt sludge
8 heat exchange between hot gases and charge
9 crude syngas
10 purification of syngas and heat utilization
11 separated water
12 gas compression
13 separation of liquid carbon dioxide
14 reactor for methanol synthesis I. $CO+2 H_2 \rightarrow CH_3OH$
15 pure methanol
16 storage of liquid carbon dioxide
17 hydrogen
18 reactor for methanol synthesis II. $CO_2+3H_2 \rightarrow CH_3OH+H_2O$
19 64 w/w % methanol, methanol:water molar ratio 1:1
20 bottled oxygen for sale
21 gas motor as required In the course of the methanol production according to the invention the starting material is fed to generator body A through 1 waste mixture charge hole. By its weight the material passes upwards in 2 pyrolysis zone and it is heated through the 8 heat exchange wall, its' bound humidity and the pyrolysis water are released and the plastics are depolymerised. The exotherm combustial processes resulting in carbon dioxide take place by the aid of oxygen introduced from the 3 water electrolyser through 4 studs. At the high temperature of about 1000° C. in the 6 reduction zone carbon monoxide and hydrogen are formed from the residual carbon containing materials upon the effect of vapour due to heat consuming procedures. At this temperature the sludge is partly melt and is exhausted at 7 sludge removal. After the sludge grid at the bottom of 6 zone the formed crude waste gases pass towards the 9 crude syngas by-bass between the outer wall of the generator body A and the inner 2 pyrolysis zone. A part of their heat content serves for the heating of the pyrolysis zone.

The chemisorption of the hydrohalides first takes place in the 10 syngas cleaning and heat utilizer part of the high temperature heterogen reactor with solid limestone filling and then in the heat utilizer furnace vapour is developed for the preparation of electric energy. Mercaptane and hydrosulphide are removed with oxyquinone and charcoal, as a side product sulphur is obtained. After further heat utilization and cooling, the purified syngas is cooled to about 30° C., and the formed or unchanged vapour is condensed from said purified syngas. The separated water is introduced, if necessary, through 11 duct to the 3 electrolysing system.

A part of the purified syngas is led to 21 gas motor if no renewing energy is available. The remaining gas is compressed in 12 compressor, then it is removed with a alkali carbonate washer and stored in liquid state in 13 and 16 containers.

The syngas containing only traces of carbon dioxide is led to 14 methanol reactor, where the 1:2 ratio of $CO-H_2$ is adjusted with 17 hydrogen derived from the electrolysis. Methanol vapours leaving the reactor are condensed by heat utilization and the residual gases, comprising $C_1$ and $C_2$ pyrolysis gases and unreacted carbon monoxide or hydrogen gases, are utilized in 21 gas motor.

The stored 16 liquid carbon dioxide is converted to methanol in 18 reactor if renewing energy is available, by which in 3 electrolyser system additional 17 hydrogen is prepared by introducing fresh water. The obtained oxygen is for sale. The 19 1:1 methanol and water vapour mixture obtained in 18 reactor is separated by selective condensation to pure methanol and water, as is recycled to the electrolyser cell.

The process is further illustrated with the following non-limiting examples.

EXAMPLE 1

A waste flow comprising 10% of sludge (30% of dry material), 70% of organic communal waste and 20% of harvest loss of forest felling site is fed to a low gas inverter generator having an upper filling hole, the bed temperature of which is 1000° C. Into the upper level of the hot layer oxygen of a purity obtained by the electrolysis of water, amounting to 30 m/m % of the raw material flow is introduced. The volume of the generator is 50 l, the ratio of height and outer diameter is 4:1. The diameter of the inner pyrolysis is 75% of the outer diameter.

The hydrochloric acid vapours are bound by transferring same from the exhaust gases through a calcium-carbonate-filled column by inner feeding, whereafter the water vapours are condensed by air cooling. Due to the small size a Lux mass is applied for the removal of hydrosulphide.

The purified crude gas is washed with a potassium hydrogen carbonate solution at a pressure of 50 bar in a column filled with Raschig rings, and it is then reacted after drop separation by passing it through tubes of a temperature of 150° C. thermostated with an oilbath, filled with a catalyst having an inner diameter of 5 mm. The reaction product is condensed by cooling. The catalyst was a mixture of potassium methyl carbonate applied on an alumina carrier and transitory metal-methyl carbonates. The obtained methanol is 35% of the weight of the charged material, its water content amounts to less than 1%. The uncondensed gases are burnt.

EXAMPLE 2

A waste flow comprising 70% of organic communal waste and 30% of autumn harvested maize stalk are fed into the lower gas inverter generator having an upper charging hole, the bed temperature of which is 1000° C. Into the upper level of the hot layer, oxygen obtained by the electrolysis of water amounting to 30 m/m % of the raw material flow, is introduced. At the same site we have added 5% of dead oil amounting to 5% of the upper waste weight flow. The volume of the generator is 50 l, the ratio of height and outer diameter is 4:1.

The diameter of the inner pyrolysis is 75% of the outer diameter. The hydrochloric acid vapours are bound by transferring same from the exhaust gases through a calcium carbonate-filled column by inner feeding, whereafter the water vapours are condensed by air cooling. Due to the small size a Lux mass is applied for the removal of hydrosulphide. The purified crude gas is washed with a potassium hydrogen carbonate solution at a pressure of 50 bar in a column filled with Raschig rings, and it is then reacted after drop separation by passing it through tubes of a temperature of 150° C. thermostated with an oilbath, filled with a catalyst having an inner diameter of 5 mm. The reaction product is condensed by cooling. The catalyst was a mixture of potassium methyl carbonate applied on an alumina carrier and transitory metal-methylcarbonates. The obtained methanol is 45% of the weight of the charged material, its water content amounts to less than 1%. The uncondensed gases are burnt.

The invention claimed is:

1. A process for the preparation of low-tar syngas, from organic wastes and converting optionally the syngas to methanol or preparing methanol from separated carbon dioxide, which comprises introducing secondary raw material into a double-flow one-body generator comprising an inner pyrolysing, oxidizing and reducing zone and converting obtained pyrolysis coke, pyrolysis water and tar formed by the aid of the heat content of gas flowing upwards in an outer gas space by blowing oxygen into a fixed bed of the pyrolysis coke, to a raw syngas comprising carbon dioxide, carbon monoxide and hydrogen, on the fixed bed of the pyrolysis coke at a temperature of 600-1200° C. and a liquid containing liquid hydrocarbons or a powder of high carbon content are optionally added in order to control the temperature, and hydrohalides are removed from the obtained raw syngas on a calcium carbonate bed at 200-700 ° C., the heat content of the raw syngas is utilized, carbon dioxide is removed, and carbon dioxide is converted to methanol by using an external hydrogen source and the obtained syngas is optionally also converted to methanol.

2. The process of claim 1, which comprises converting the fed waste to syngas comprising carbon monoxide, carbon dioxide and hydrogen at a bed temperature of 1000° C., by injecting oxygen at a pressure of 0.9-2 bar and water vapor derived from drying and pyrolysis in the reactor space.

3. The process of claim 1, which comprises applying a temperature of 650° C. in the reactor removing hydrohalides.

4. The process of claim 1, which comprises injecting hydrocarbon containing liquid wastes into the reactor space of the generator for controlling temperature.

5. The process of claim 1, which comprises injecting powdered wastes of high carbon content into the pyrolysis reactor space of the generator for controlling temperature.

6. The process of claim 1, which comprises ensuring the electric energy needed for the operation of the system by utilizing a part of the purified gases in the gas motor.

7. The process of claim 1, which comprises isolating the carbon dioxide content of the raw syngas by an absorption desorption process, storing it in liquid state and converting it to methanol by adding hydrogen.

8. The process of claim 1, which comprises carrying out the methanol synthesis in a catalytic reactor at a pressure of 15-75 bar and at a temperature range of 100-260° C.

9. The process of claim 1, wherein the secondary raw material comprises solid communal waste, sludge or biomass waste.

10. The process of claim 1, wherein the obtained pyrolysis coke, pyrolysis water and tar are converted to the raw syngas comprising carbon dioxide, carbon monoxide and hydrogen, on the fixed bed of the pyrolysis coke at a temperature of about 1000° C.

11. The process of claim 1, wherein the gas flowing upwards in an outer gas space is the raw syngas.

12. The process of claim 1, wherein the secondary raw material is not dry prior to being introduced into the generator.

\* \* \* \* \*